United States Patent
Amos

(10) Patent No.: US 9,408,733 B2
(45) Date of Patent: Aug. 9, 2016

(54) ROTATABLE CONNECTION BETWEEN A TUBULAR MEMBER AND AN ELONGATE WIRE OF A CATHETER

(76) Inventor: Michael Devon Amos, Boston, MA (US)

(*) Notice: Subject to any disclaimer, the term of this patent is extended or adjusted under 35 U.S.C. 154(b) by 599 days.

(21) Appl. No.: 12/971,078

(22) Filed: Dec. 17, 2010

(65) Prior Publication Data

US 2011/0160739 A1 Jun. 30, 2011

Related U.S. Application Data

(60) Provisional application No. 61/291,342, filed on Dec. 30, 2009.

(51) Int. Cl.
| | |
|---|---|
| *A61F 11/00* | (2006.01) |
| *A61F 2/95* | (2013.01) |
| *A61M 25/06* | (2006.01) |
| *A61M 27/00* | (2006.01) |
| *A61M 25/00* | (2006.01) |
| *A61M 25/01* | (2006.01) |

(52) U.S. Cl.
CPC .............. *A61F 2/95* (2013.01); *A61M 25/0662* (2013.01); *A61F 2002/9511* (2013.01); *A61M 27/008* (2013.01); *A61M 2025/0004* (2013.01); *A61M 2025/0046* (2013.01); *A61M 2025/0062* (2013.01); *A61M 2025/0175* (2013.01); *A61M 2025/0183* (2013.01); *A61M 2025/0681* (2013.01)

(58) Field of Classification Search
CPC ............. A61F 2/95; A61F 2002/9511; A61M 25/0662; A61M 2025/0046; A61M 2025/0183; A61M 27/008; A61M 2025/0681; A61M 2025/0004; A61M 2025/0175; A61M 2025/0062

USPC ................................ 604/8; 606/108; 623/1.11
See application file for complete search history.

(56) References Cited

U.S. PATENT DOCUMENTS

| | | | |
|---|---|---|---|
| 2,212,334 | A | 8/1940 | Wallerich |
| 2,393,003 | A | 1/1946 | Smith |
| 3,100,490 | A | 8/1963 | Desautels |
| 3,332,424 | A | 7/1967 | Minteer |
| 3,421,509 | A | 1/1969 | Fiore |
| 3,592,197 | A | 7/1971 | Cohen |
| 3,783,453 | A | 1/1974 | Bolie |
| 3,908,635 | A | 9/1975 | Viek |
| 3,938,529 | A | 2/1976 | Gibbons |
| 3,995,642 | A | 12/1976 | Adair |
| 4,212,304 | A | 7/1980 | Finney |

(Continued)

FOREIGN PATENT DOCUMENTS

| | | | |
|---|---|---|---|
| CA | 1112119 | A | 11/1981 |
| DE | 3345612 | A1 | 6/1985 |

(Continued)

*Primary Examiner* — Richard Louis
(74) *Attorney, Agent, or Firm* — Kacvinsky Daisak Bluni PLLC

(57) ABSTRACT

A rotatable connection between a tubular member and an elongate wire of a catheter for allowing rotational movement of the tubular member relative to the elongate wire. The rotatable connection includes a first tube secured to the tubular member and a second tube secured to the elongate wire. The second tube is disposed around the first tube and rotatable relative to the first tube. The longitudinal axis of the tubular member is offset from the longitudinal axis of the elongate wire to allow a guidewire to extend through the tubular member and along the side of the elongate wire.

17 Claims, 6 Drawing Sheets

(56) References Cited

U.S. PATENT DOCUMENTS

| | | | |
|---|---|---|---|
| 4,225,979 A | 10/1980 | Rey et al. | |
| 4,242,304 A | 12/1980 | Ryder | |
| 4,248,214 A | 2/1981 | Hannah et al. | |
| 4,307,723 A | 12/1981 | Finney | |
| 4,334,327 A | 6/1982 | Lyman et al. | |
| 4,382,445 A | 5/1983 | Sommers | |
| 4,434,797 A | 3/1984 | Silander | |
| 4,474,569 A | 10/1984 | Newkirk | |
| 4,484,585 A | 11/1984 | Baier | |
| 4,500,313 A | 2/1985 | Young | |
| 4,531,933 A | 7/1985 | Norton et al. | |
| 4,545,373 A | 10/1985 | Christoudias | |
| 4,568,338 A | 2/1986 | Todd | |
| 4,592,341 A | 6/1986 | Omagari et al. | |
| 4,610,657 A | 9/1986 | Densow | |
| 4,643,716 A | 2/1987 | Drach | |
| 4,645,493 A | 2/1987 | Ferrando et al. | |
| 4,671,795 A | 6/1987 | Mulchin | |
| 4,684,369 A | 8/1987 | Wildemeersch | |
| 4,699,611 A | 10/1987 | Bowden | |
| 4,713,049 A | 12/1987 | Carter | |
| 4,738,667 A | 4/1988 | Galloway | |
| 4,747,833 A | 5/1988 | Kousai et al. | |
| 4,755,175 A | 7/1988 | Nilsson | |
| 4,762,128 A | 8/1988 | Rosenbluth | |
| 4,783,454 A | 11/1988 | Liu | |
| 4,784,651 A | 11/1988 | Hickey | |
| 4,787,884 A | 11/1988 | Goldberg | |
| 4,790,809 A | 12/1988 | Kuntz | |
| 4,790,810 A | 12/1988 | Pugh, Jr. et al. | |
| 4,813,925 A | 3/1989 | Anderson, Jr. et al. | |
| 4,820,262 A | 4/1989 | Finney | |
| 4,822,333 A | 4/1989 | Lavarenne | |
| 4,824,435 A | 4/1989 | Giesy et al. | |
| 4,832,055 A | 5/1989 | Palestrant | |
| 4,874,360 A | 10/1989 | Goldberg et al. | |
| 4,886,065 A | 12/1989 | Collins, Jr. | |
| 4,913,141 A | 4/1990 | Hillstead | |
| 4,913,683 A | 4/1990 | Gregory | |
| 4,931,037 A | 6/1990 | Wetterman | |
| 4,950,228 A | 8/1990 | Knapp, Jr. et al. | |
| 4,955,858 A | 9/1990 | Drews | |
| 4,957,479 A | 9/1990 | Roemer | |
| 4,963,129 A | 10/1990 | Rusch | |
| 4,973,301 A | 11/1990 | Nissenkorn | |
| 4,990,133 A | 2/1991 | Solazzo | |
| 4,994,066 A | 2/1991 | Voss | |
| 5,019,085 A | 5/1991 | Hillstead | |
| 5,019,102 A | 5/1991 | Hoene | |
| 5,052,998 A | 10/1991 | Zimmon | |
| 5,098,374 A | 3/1992 | Othel-Jacobsen et al. | |
| 5,116,309 A | 5/1992 | Coll | |
| 5,141,502 A | 8/1992 | Macaluso, Jr. | |
| 5,147,370 A | 9/1992 | McNamara et al. | |
| 5,152,749 A | 10/1992 | Giesy et al. | |
| 5,160,341 A | 11/1992 | Brenneman et al. | |
| 5,234,437 A | 8/1993 | Sepetka | |
| 5,250,071 A | 10/1993 | Palermo | |
| 5,261,916 A | 11/1993 | Engelson | |
| 5,267,958 A | 12/1993 | Buchbinder et al. | |
| 5,282,784 A | 2/1994 | Willard | |
| 5,295,954 A | 3/1994 | Sachse | |
| 5,304,195 A | 4/1994 | Twyford, Jr. et al. | |
| 5,304,198 A | 4/1994 | Samson | |
| 5,320,604 A | 6/1994 | Walker et al. | |
| 5,322,501 A | 6/1994 | Mahmud-Durrani | |
| 5,324,259 A | 6/1994 | Taylor et al. | |
| 5,334,185 A | 8/1994 | Giesy et al. | |
| 5,346,467 A | 9/1994 | Coll | |
| 5,348,537 A | 9/1994 | Wiesner et al. | |
| 5,354,263 A | 10/1994 | Coll | |
| 5,364,340 A | 11/1994 | Coll | |
| 5,364,354 A | 11/1994 | Walker et al. | |
| 5,364,376 A | 11/1994 | Horzewski et al. | |
| 5,372,600 A | 12/1994 | Beyar et al. | |
| 5,391,155 A | 2/1995 | Sachse | |
| 5,399,165 A | 3/1995 | Paul, Jr. | |
| 5,401,257 A | 3/1995 | Chevalier, Jr. et al. | |
| 5,405,378 A | 4/1995 | Strecker | |
| 5,407,435 A | 4/1995 | Sachse | |
| 5,409,468 A | 4/1995 | Sachse | |
| 5,454,788 A | 10/1995 | Walker et al. | |
| 5,458,615 A | 10/1995 | Klemm et al. | |
| 5,476,505 A | 12/1995 | Limon | |
| 5,480,434 A | 1/1996 | Eckstein et al. | |
| 5,484,409 A | 1/1996 | Atkinson et al. | |
| 5,496,344 A | 3/1996 | Kanesaka et al. | |
| 5,540,236 A | 7/1996 | Ginn | |
| 5,578,009 A | 11/1996 | Kraus et al. | |
| 5,599,291 A | 2/1997 | Balbierz et al. | |
| 5,639,274 A | 6/1997 | Fischell et al. | |
| 5,645,533 A | 7/1997 | Blaeser et al. | |
| 5,653,748 A | 8/1997 | Strecker | |
| 5,669,880 A | 9/1997 | Solar | |
| 5,676,654 A | 10/1997 | Ellis et al. | |
| 5,681,274 A | 10/1997 | Perkins et al. | |
| 5,690,642 A | 11/1997 | Osborne et al. | |
| 5,693,015 A | 12/1997 | Walker et al. | |
| 5,776,099 A | 7/1998 | Tremulis | |
| 5,921,952 A | 7/1999 | Desmond, III et al. | |
| 5,921,971 A | 7/1999 | Agro et al. | |
| 6,093,176 A * | 7/2000 | Dennis | 604/256 |
| 6,095,990 A | 8/2000 | Parodi | |
| 6,159,177 A | 12/2000 | Amos, Jr. et al. | |
| 6,159,195 A | 12/2000 | Ha et al. | |
| 6,248,100 B1 | 6/2001 | de Toledo et al. | |
| 6,264,624 B1 | 7/2001 | Desmond, III et al. | |
| 6,540,719 B2 | 4/2003 | Bigus et al. | |
| 6,562,024 B2 | 5/2003 | Alvarez de Toledo et al. | |
| 7,087,038 B2 | 8/2006 | Lee | |
| 7,297,134 B2 | 11/2007 | Krivoruchko | |
| 7,326,224 B2 | 2/2008 | Houde et al. | |
| 7,550,002 B2 | 6/2009 | Goto et al. | |
| 7,879,080 B2 | 2/2011 | Sato | |
| 2001/0018574 A1 | 8/2001 | Toledo et al. | |
| 2002/0004676 A1* | 1/2002 | Wallace et al. | 623/1.12 |
| 2004/0039373 A1 | 2/2004 | Harding et al. | |
| 2005/0085891 A1* | 4/2005 | Goto et al. | 623/1.11 |
| 2005/0085892 A1* | 4/2005 | Goto et al. | 623/1.12 |
| 2005/0187602 A1 | 8/2005 | Eidenschink | |
| 2005/0187603 A1 | 8/2005 | Eidenschink et al. | |
| 2006/0212009 A1 | 9/2006 | Accisano, III et al. | |
| 2007/0293929 A1 | 12/2007 | Aoba et al. | |
| 2008/0262506 A1* | 10/2008 | Griffin et al. | 606/108 |
| 2009/0143849 A1 | 6/2009 | Ozawa et al. | |
| 2009/0204197 A1* | 8/2009 | Dorn et al. | 623/1.11 |
| 2009/0312829 A1 | 12/2009 | Aoba et al. | |
| 2010/0076541 A1* | 3/2010 | Kumoyama | 623/1.11 |
| 2010/0191193 A1 | 7/2010 | Pajunk et al. | |

FOREIGN PATENT DOCUMENTS

| | | |
|---|---|---|
| DE | 3919740 A1 | 12/1990 |
| DE | 102007029229 | 12/2008 |
| GB | 2 018 600 A | 10/1979 |
| WO | WO 93/00126 A1 | 1/1993 |
| WO | 93/16642 | 9/1993 |
| WO | WO 99/08740 | 2/1999 |
| WO | 2005/115524 | 12/2005 |

* cited by examiner

ROTATABLE CONNECTION BETWEEN A TUBULAR MEMBER AND AN ELONGATE WIRE OF A CATHETER

CROSS REFERENCE TO RELATED APPLICATIONS

This application claims the benefit of U.S. Provisional Application Ser. No. 61/291,342, filed Dec. 30, 2009, the entire disclosure of which is incorporated herein by reference.

TECHNICAL FIELD

The disclosure is directed to a rotatable connection for a medical device. More particularly, the disclosure is directed to a rotatable connection between a tubular member and an elongate wire of a catheter for allowing rotational movement of the tubular member relative to the elongate wire.

BACKGROUND

Medical devices, such as catheters, are widely used in various medical procedures to access remote anatomical locations and/or deploy therapeutic devices. One exemplary catheter system is a drainage catheter delivery system configured to delivery a drainage catheter (e.g., stent) to a body lumen, such as a lumen of the biliary tree or a ureter. One embodiment of a drainage catheter delivery system, disclosed in U.S. Pat. No. 6,562,024, the disclosure of which is incorporated herein by reference, includes a guide catheter including a distal tubular portion and a proximal wire portion attached to the distal tubular portion. The guide catheter, including at least a portion of the distal tubular portion and at least a portion of the proximal wire portion may be slidably disposed in a lumen of a push catheter of the drainage catheter delivery system.

In some instances, the proximal wire portion of the guide catheter, which may share a lumen of the push catheter with a guidewire, may become twisted and/or entangled with the guidewire as the system moves through numerous turns during delivery of the drainage catheter to a target location in the anatomy of a patient.

Therefore, a need remains to provide a medical device construction configured to allow components of the medical device to rotate relative to other components of the medical device in order to prevent entanglement of the wire portion of a catheter with a guidewire.

SUMMARY

The disclosure is directed to several alternative designs and configurations of medical device structures and assemblies including locking mechanisms.

Accordingly, one illustrative embodiment is a catheter assembly including a handle assembly, a first tubular member coupled to the handle assembly and extending distally therefrom, a second tubular member disposed within a distal portion of the lumen of the first tubular member, and an elongate wire coupled to the second tubular member at a rotatable connection. The elongate wire extends proximally from the second tubular member through a proximal portion of the lumen of the first tubular member. The rotatable connection allows the second tubular member to rotate independently of the elongate wire. The rotatable connection may include a first tube having a distal portion fixedly secured to the second tubular member and a second tube fixedly secured to the elongate wire. The second tube may be disposed around a proximal portion of the first tube and being rotatable relative to the first tube.

Another embodiment is a drainage catheter delivery system including a handle assembly, a push catheter extending distally from the handle assembly, a guide catheter disposed in the lumen of the push catheter and having a distal portion extending distal of the distal end of the push catheter, and a drainage catheter disposed on a portion of the tubular member of the guide catheter extending distal of the distal end of the push catheter. The guide catheter includes a tubular member and an elongate wire coupled to the tubular member at a rotatable connection, wherein the rotatable connection allows the tubular member of the guide catheter to rotate independently of the elongate wire of the guide catheter. The rotatable connection may include a first tube having a distal portion fixedly secured to the second tubular member and a second tube fixedly secured to the elongate wire. The second tube may be disposed over a proximal portion of the first tube and rotatable relative to the first tube. In some instances, the central longitudinal axis of the elongate wire is offset from the central longitudinal axis of the tubular member.

Yet another embodiment is a catheter assembly including an elongate tubular member, an elongate wire, and a rotatable connection rotatably coupling the elongate wire to the elongate tubular member. The rotatable connection includes a first tube having a distal portion disposed in the lumen of the elongate tubular member and a proximal portion extending proximal of the proximal end of the elongate tubular member, and a second tube being fixedly attached to the elongate wire. The second tube is disposed around the proximal portion of the first tube and is rotatable relative to the first tube.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
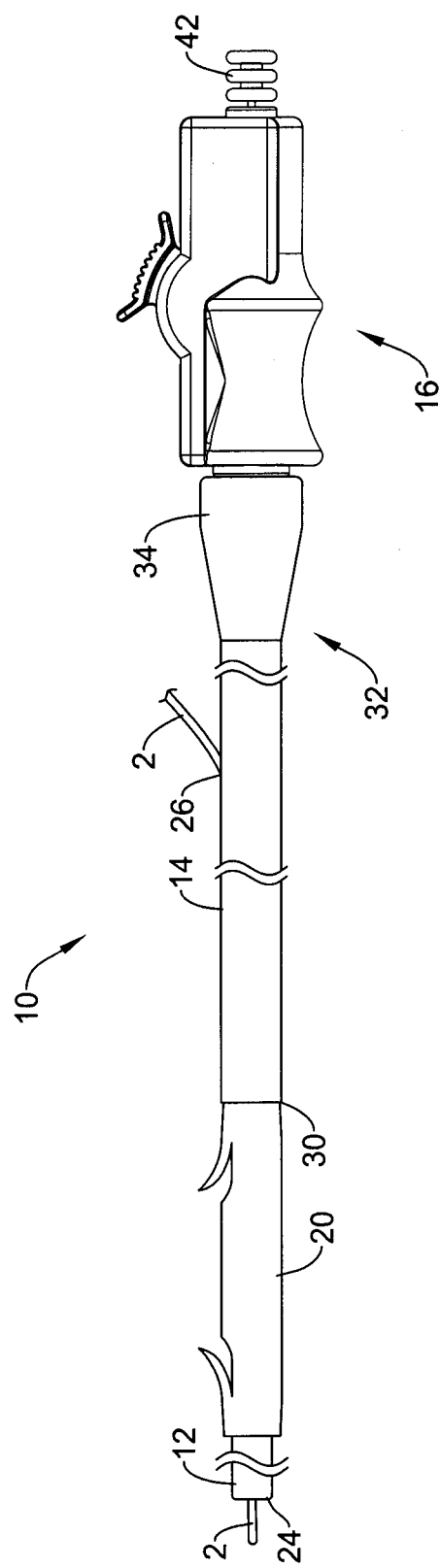
FIG. 1 is a plan view of an exemplary drainage catheter delivery system including a handle assembly having a locking mechanism.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
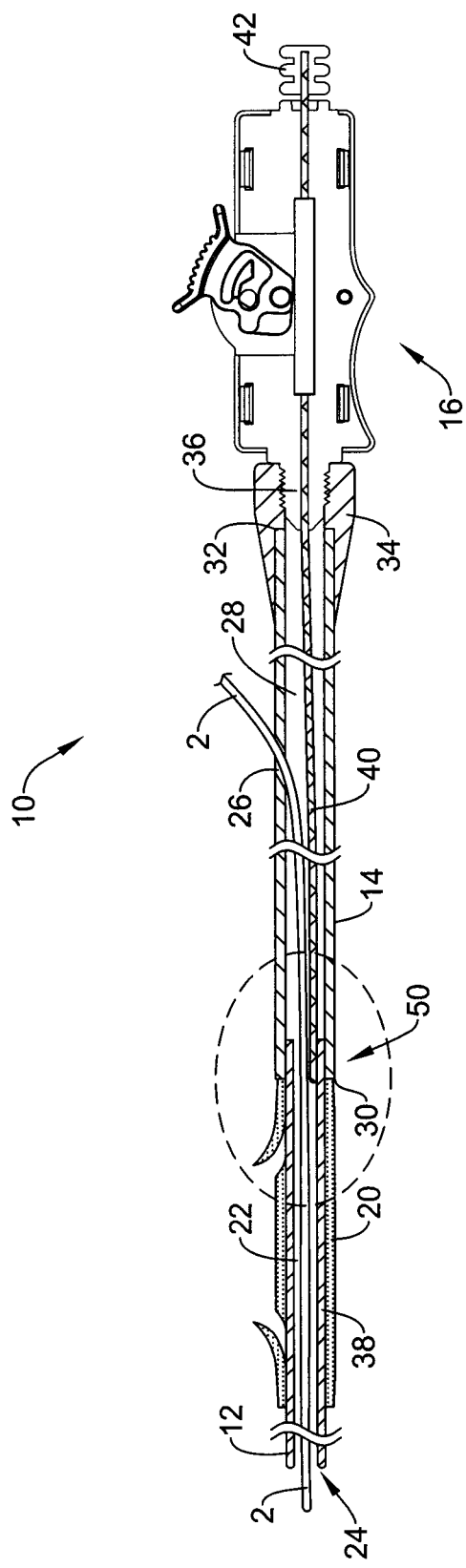
FIG. 2 is a longitudinal cross-sectional view of the drainage catheter delivery system of FIG. 1.

Referring now to FIGS. 1 and 2, there is shown an exemplary medical device, illustrated as a drainage catheter delivery system 10 for delivering a drainage catheter or stent 20 to an anatomical location, such as in a lumen of the biliary tree or a ureter. The drainage catheter 20 may be used to bypass or drain an obstructed lumen and can be configured for long-term positioning within the lumen. It should be understood that the terms "drainage catheter" and "stent" can be used interchangeably with reference to these applications.

The drainage catheter delivery system 10 is designed for use with a conventional guidewire 2 and may include a drainage catheter 20, a guide catheter 12, a push catheter 14, and a handle assembly 16. The guidewire 2 may extend into a lumen 22 of the guide catheter 12 through a distal guidewire port 24 and out a proximal guidewire port 26 in a sidewall of the push catheter 14, providing the drainage catheter delivery system 10 with single-operator-exchange (SOE) capabilities.

The guide catheter 12 is slidably disposed in the lumen 28 of the push catheter 14 and extends distally from the distal end of the push catheter 14. The drainage catheter 20 is positioned on a distal portion of the guide catheter 12 located distal of the push catheter 14 and may abut the distal end 30 of the push catheter 14. The drainage catheter delivery system 10 may include a means for releasably connecting the push catheter 14 to the drainage catheter 20. When the drainage catheter 20 has been properly placed, the drainage catheter 20 may be disconnected from the push catheter 14 such that the drainage catheter 20 remains in the lumen when the push catheter 14 is withdrawn. For example, the drainage catheter 20 may be disconnected from the push catheter 14 by withdrawing the guide catheter 12 proximally relative to the drainage catheter 20 and the push catheter 14. Some exemplary drainage catheter delivery systems including means for releasably connecting the push catheter 14 to the drainage catheter 20 are disclosed in U.S. Pat. Nos. 5,921,952 and 6,562,024, the disclosures of which are incorporated herein by reference. For example, a suture (not shown) attached to the push catheter 14 may be threaded around a portion of the drainage catheter 20 and the guide catheter 12. As the guide catheter 12 is moved longitudinally in a proximal direction relative to the drainage catheter 20 and the push catheter 14, the suture may be freed from the guide catheter 12 and the drainage catheter 20, releasing the drainage catheter 20.

The proximal end 32 of the push catheter 14 may be attached to the handle assembly 16. For example, the proximal end 32 may include a female luer lock connector 34 threadably coupled to a threaded male connector 36 of the handle assembly 16. It is understood, however, that the push catheter 14 may be attached to the handle assembly 16 and extend distally therefrom by other means, such as adhesive bonding, welding, friction fit, interlocking fit, or other suitable means.

The guide catheter 12 may include a distal tubular portion 38 and a proximal elongate wire 40, such as a pull wire, coupled to the distal tubular portion 38. In some instances, the elongate wire 40 may be a wire, filament, thread, portion of a catheter wall, fabric, web, or similar elongate structure. The elongate wire 40 may be coupled to the distal tubular portion 38 at a rotatable connection 50 which allows rotatable movement between the tubular portion 38 and the elongate wire 40 of the guide catheter 12. The elongate wire 40 may extend through the lumen 28 of the push catheter 14 to the handle assembly 16. In some embodiments, the elongate wire 40 may extend through the handle assembly 16 to a location proximal of the handle assembly 16. The proximal end of the elongate wire 40 may terminate at a knob 42 which may be grasped by an operator to manipulate the guide catheter 12.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

Figure 3:
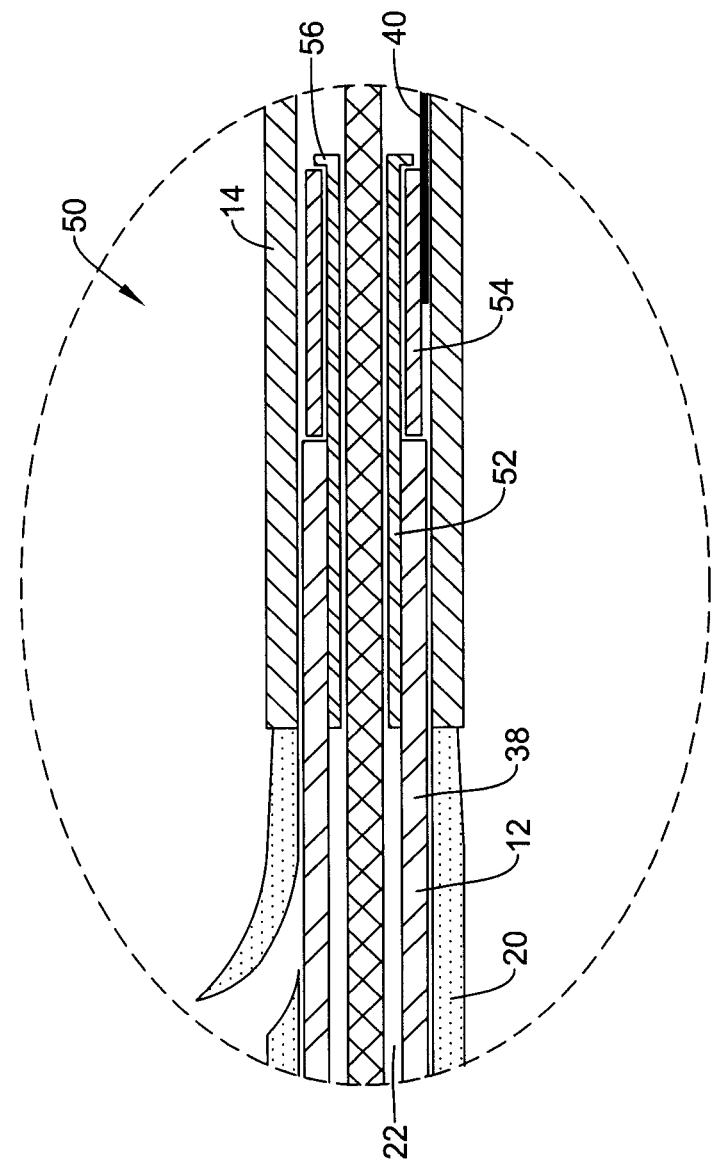
FIG. 3 is an enlarged view of a portion of the drainage catheter delivery system of FIG. 2 illustrating a rotatable connection between a tubular member and an elongate wire of a catheter assembly.

FIG. 3 is an enlarged cross-sectional view of the rotatable connection 50 between the tubular member 38 and the elongate wire 40 of the guide catheter 12. The rotatable connection 50 may include a first tube 52 rotatably coupled to a second tube 54. For instance, the first tube 52 may extend through the lumen of the second tube 54 such that the second tube 54 may freely revolve around the first tube 52.

Each of the first tube 52 and the second tube 54 may be formed of any desired material for use with medical devices. Some suitable materials include metal, metal alloy, metal-polymer composite, combinations thereof, and the like, or any other suitable material. Some examples of suitable metals and metal alloys include stainless steel, such as 304V, 304L, and 316LV stainless steel; mild steel; nickel-titanium alloy, such as linear-elastic and/or super-elastic nitinol; other nickel alloys; platinum enriched stainless steel; combinations thereof; and the like; or any other suitable material. In some instances, the first tube 52 and/or the second tube 54 may be a stainless steel hypotube. Some examples of suitable polymers may include polytetrafluoroethylene (PTFE), ethylene tetrafluoroethylene (ETFE), fluorinated ethylene propylene (FEP), polyoxymethylene (POM), polyether block ester, polyurethane, polypropylene (PP), polyvinylchloride (PVC), polyether-ester, ether or ester-based copolymers, polyamide, elastomeric polyamides, block polyamide/ethers, polyether block amide (PEBA), ethylene vinyl acetate copolymers (EVA), silicones, polyethylene (PE) including high-density polyethylene and linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), nylon, nylon-12, polyolefin, polystyrene, or other suitable materials, or mixtures, combinations, copolymers thereof, polymer/metal composites, and the like.

The first tube 52 may be fixedly secured to the tubular member 38, while the second tube 54 may be fixedly secured to the elongate wire 40. For instance, a distal portion of the first tube 52 may extend into the lumen 22 of the tubular member 38 from the proximal end of the tubular member 38 such that a distal end of the first tube 52 is located distal of the proximal end of the tubular member 38. In other embodiments, however, the first tube 52 may be fixedly secured to the tubular member 38 in another fashion. For example, the first tube 52 may extend over a proximal portion of the tubular member 38 and be attached thereto. In some embodiments, the first tube 52 may be sized and configured to provide an interference fit or interlocking fit with the tubular member 38. For instance, the first tube 52 may have an outer diameter which is greater than the inner diameter of the tubular member 38 to provide an interference fit and/or the first tube 52 may include one or more annular burrs or projections which engage the inner surface of the tubular member 38. Additionally or alternatively, the first tube 52 may be welded or bonded, such as thermally or adhesively bonded, to the tubular member 38.

The second tube 54 may be fixedly secured to a distal end of the elongate wire 40 such that the elongate wire 40 extends proximally from the second tube 54. For instance, a distal portion of the elongate wire 40 may be positioned along an outer surface of the second tube 54 and welded or bonded, such as thermally or adhesively bonded, to the second tube 54. In some instances, the elongate wire 40 may loop through the wall of the second tube 54 or may be attached to the inside of the second tube 54. In some instances, the elongate wire 40 may be a portion of the wall of the second tube 54 extending proximally from a tubular section of the second tube 54.

The second tube 54 may be disposed around a proximal portion of the first tube 52 such that the second tube 54 may be rotated relative to the first tube 52. As shown in FIG. 3, the first tube 52 may include a flared end or a flange 56 located at or near the proximal end of the first tube 52. The second tube 54 may be located between the proximal end of the tubular member 38 and the flange 56 of the first tube 52 such that the second tube 54 is restrained from longitudinal movement in either the proximal or distal direction.

In some embodiments, the interface between the outer surface of the first tube 52 and the inner surface of the second tube 54 may have a low coefficient of friction to reduce rotational resistance between the first tube 52 and the second tube 54. For instance, in some embodiments, the outer surface of the first tube 52 and/or the inner surface of the second tube 54 may be coated with a lubricious coating providing a low coefficient of friction between the outer surface of the first tube 52 and the inner surface of the second tube 54 to aid in reducing resistance in rotational movement between the first tube 52 and the second tube 54. Some suitable coating materials which may provide a low coefficient of friction include silicone or a fluoropolymer such as polytetrafluoroethylene (PTFE), ethylene tetrafluoroethylene (ETFE) or fluorinated ethylene propylene (FEP). In some instances, the outer surface of the first tube 52 and/or the inner surface of the second tube 54 may include nibs, bumps, ridges, grooves or other surface characteristics to reduce the contact area between the first and second tubes 52, 54. In other embodiments, the first tube 52 and the second tube 54 may be formed to have different cross-sectional shapes to reduce the contact area and/or number of contact points between the first and second tubes 52, 54. For example, the first tube 52 may have a square cross-sectional shape while the second tube 54 may have a circular cross-sectional shape. Thus, the first tube 52 would contact the inner surface of the second tube 54 at discrete contact points to reduce the contact area between the first and second tubes 52, 54.

Figure 4:
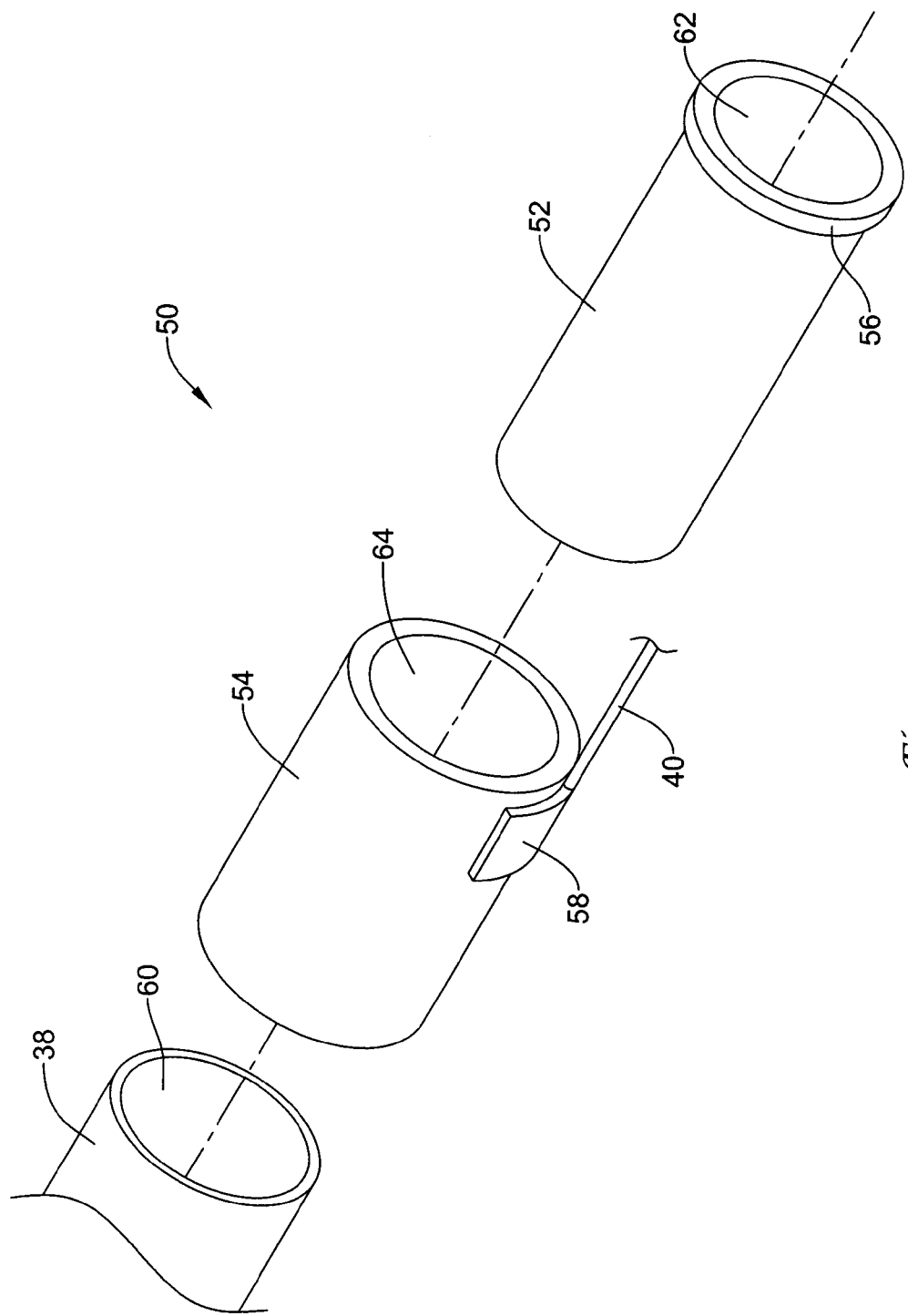
FIG. 4 is an exploded perspective view of components of the rotatable connection between the tubular member and the elongate wire of the catheter assembly of the drainage catheter delivery system of FIG. 1.
Figure 5:
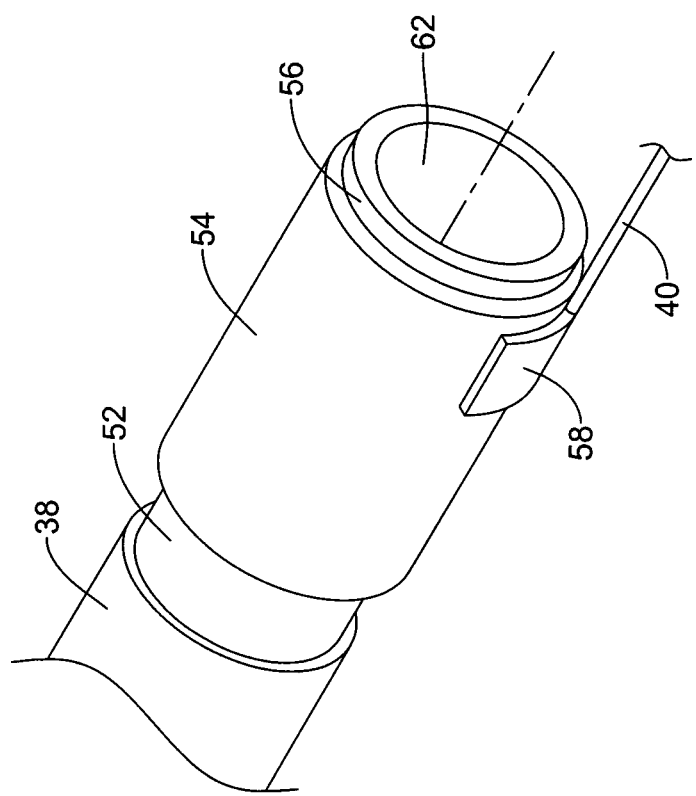
FIG. 5 is a perspective view of the rotatable connection between the tubular member and the elongate wire of the catheter assembly of the drainage catheter delivery system of FIG. 1.

FIGS. 4 and 5 further illustrate the rotatable connection 50 between the tubular member 38 and the elongate wire 40 of the guide catheter 12. As shown in the Figures, the central longitudinal axis of the tubular member 38 may be coaxial with both the central longitudinal axis of the first tube 52 and the central longitudinal axis of the second tube 54. The elongate wire 40 may be secured to the second tube 54 at a location around the perimeter of the second tube 54, thus the central longitudinal axis of the elongate wire 40 may be offset from the central longitudinal axis of the tubular member 38. For instance, the elongate wire 40 may be fixedly secured to the annular wall of the second tube 54. As shown in FIGS. 4 and 5, the elongate wire 40 may include a saddle portion 58 having an arcuate shape which generally follows an arcuate surface of the second tube 54. For instance, the saddle portion 58 may be located on the exterior of the second tube 54 such that a concave surface of the saddle portion 58 is in contact with a convex outer surface of the second tube 54. The saddle portion 58 may extend partially around the circumference of the second tube 54. However, in other embodiments, the saddle portion 58 may be located in the interior of the second tube. The saddle portion 58 may be a unitary portion of the elongate wire 40 or the saddle portion 58 may be a separate piece affixed to the elongate wire 40 by welding, soldering, bonding, or the like. As discussed above, the elongate wire 40 may be attached and/or extend from the second tube 54 in other fashions. For example, the elongate wire 40 may loop through the wall of the second tube 54 or may be attached to the inside of the second tube 54. In some instances, the elongate wire 40 may be a portion of the wall of the second tube 54 extending proximally from a tubular section of the second tube 54.

The first tube 52 may have an inner diameter sized to slidably receive the guidewire 2 through the lumen 62 of the first tube 52. Thus, as the guidewire 2 extends proximally of the rotatable connection 50, the guidewire 2 may extend along the side of the elongate wire 40 of the guide catheter 12.

The first tube 52 may have an outer diameter less than the inner diameter of the second tube 54, providing a clearance fit between the first tube 52 and the second tube 54 when the first tube 52 is positioned through the lumen 64 of the second tube 54. The clearance between the outer diameter of the first tube 52 and the inner diameter of the second tube 54 may aid in rotational movement between the first tube 52 and the second tube 54. The flange 56 of the first tube 52 may have an outer diameter greater than the inner diameter of the second tube 54 to prevent the second tube 54 from sliding off the proximal end of the first tube 52. With the second tube 54 positioned between the flange 56 and the proximal end of the tubular member 38, the second tube 54 may be restrained from being disconnected from the first tube 52.

Furthermore, the first tube 52 may have a length greater than the length of the second tube 54 such that the second tube 54 is positioned around a proximal portion of the first tube 52 while a distal portion of the first tube 52 extends into the lumen 60 of the tubular member 38 of the guide catheter 12. The flange 56 of the first tube 52 may proximal of and/or abut the proximal end of the second tube 54.

During a medical procedure, the drainage catheter delivery system 10 may be advanced to a target location in the anatomy of a patient. For instance, the drainage catheter delivery system 10 may be advanced over the guidewire 2 to a target location. In some instances, the drainage catheter delivery system 10 may be tracked over the guidewire 2 as the drainage catheter delivery system 10 is advanced through a working channel of an endoscope. The guidewire 2 may pass through the lumen 22 of the guide catheter 12 and the lumen 28 of the push catheter 14 and exit through the proximal guidewire port 26 of the push catheter 14.

As the drainage catheter delivery system 10 is advanced distally, the drainage catheter 20, guide catheter 12 and push catheter 14 may move through numerous turns in the working channel of the endoscope as the drainage catheter delivery system 10 follows the patient's anatomy. As the components of the drainage catheter delivery system 10 navigate the curved pathway, one or more components, or portions thereof, may seek to rotate relative to one or more components, or portions thereof. For instance, in some cases the drainage catheter 20 may have a curved shape to assist in conforming to the anatomy of a bile duct. Due to the curved shape of the drainage catheter 20, the drainage catheter 20 may rotate inside the working channel of the endoscope as the drainage catheter 20 is advanced distally. In some instances, the drainage catheter 20 may rotate as much as one, two, three or more complete revolutions as the drainage catheter 20 is delivered to the target location. The tubular member 38 of the guide catheter 12, on which the drainage catheter 20 is positioned, may tend to rotate with the drainage catheter 20. The rotatable connection 50 between the distal tubular member 38 and the proximal elongate wire 40 of the guide catheter 14 may allow the tubular member 38 to freely rotate relative to the elongate wire 40, thus not twisting or entangling the elongate wire 40 with the guidewire 2. Furthermore, in some instances where the drainage catheter 20 is releasably attached to the push catheter 14, the push catheter 14 and thus the guidewire 2 may tend to rotate around the elongate wire 40 during distal advancement of the drainage catheter delivery system 10 through the anatomy. The rotatable connection 50 between the distal tubular member 38 and the proximal elongate wire 40 of the guide catheter 14 may allow the second tube 54 of the rotatable connection 50 to freely rotate relative to the first tube 52 of the rotatable connection 50, thus not twisting or entangling the elongate wire 40 with the guidewire 2.

When the drainage catheter 20 has been positioned at the target location in a lumen, the operator may then withdraw the guide catheter 12 proximally relative to the push catheter 14 and the handle assembly 16. For instance, the operator may grasp the knob 42 with one hand and grab the handle assembly 16 with another hand, then pull the knob 42 proximally away from the handle assembly 16 to withdraw the guide catheter 12. The force necessary to pull the elongate wire 40 proximally relative to the push catheter 14, and thus withdraw the guide catheter 12 from the drainage catheter 20, may be greatly reduced compared to the force necessary if the elongate wire 40 were twisted or entangled with the guidewire 2.

It is noted that the handle assembly 16 may have other configurations, such as a trigger grip or other conventional configuration, which may be manipulated to withdraw the guide catheter 12 from the drainage catheter 20 or otherwise actuate deployment of the drainage catheter 20.

Withdrawing the guide catheter 12 proximally relative to the push catheter 14 and the handle assembly 16 may release the drainage catheter 20 from the guide catheter 12 and push catheter 14 in order to deploy the drainage catheter 20 at the target location. For instance, if a releasing means is utilized which releasably connects the push catheter 14 to the drainage catheter 20 as disclosed in U.S. Pat. Nos. 5,921,952 and 6,562,024, the disclosures of which are incorporated herein by reference, proximal longitudinal movement of the guide catheter 12 such that the distal end of the guide catheter 12 is proximal of the distal end of the push catheter 14 will release the drainage catheter 20 from the push catheter 14 for deployment in the lumen. The drainage catheter delivery system 10 may then be withdrawn.

Figure 6:
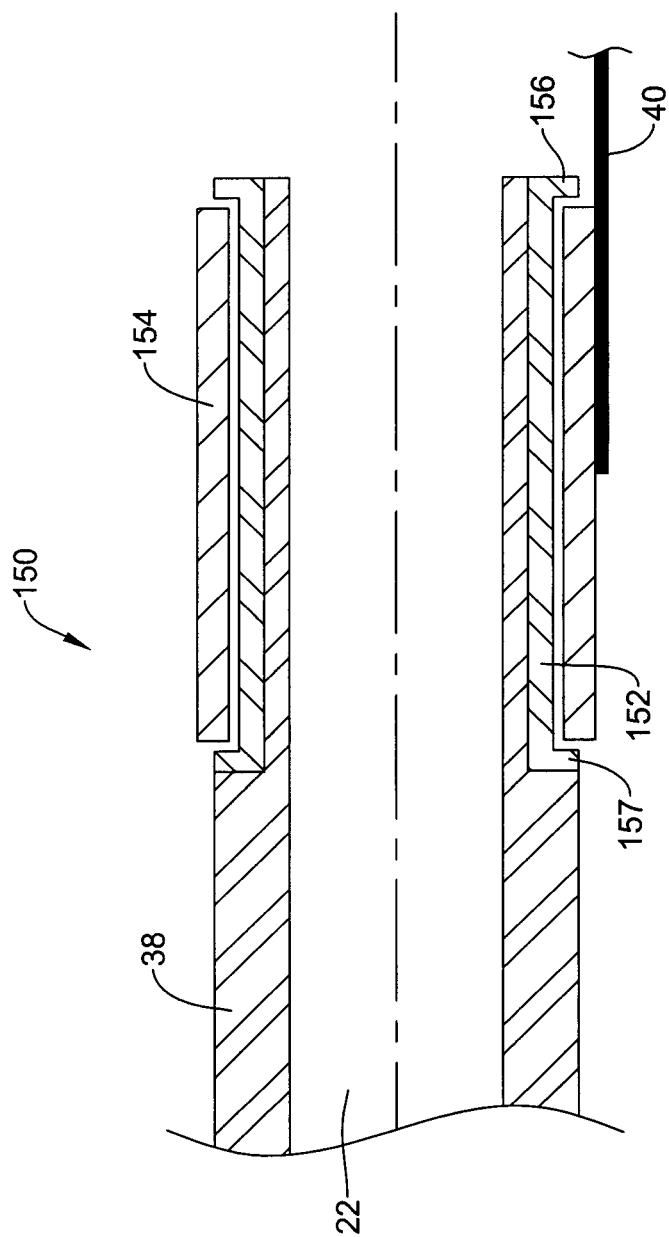
FIG. 6 is a longitudinal cross-sectional view of an alternative embodiment of a rotatable connection between a tubular member and an elongate wire of a catheter assembly.

Another embodiment of a rotatable connection 150 which may be used to rotatably couple the tubular member 38 of the guide catheter 12 to the elongate wire 40 of the guide catheter 12 is illustrated in FIG. 6. The rotatable connection 150 may include a first tube 152 rotatably coupled to a second tube 154. For instance, the first tube 152 may extend through the lumen of the second tube 154 such that the second tube 154 may freely revolve around the first tube 152. Each of the first tube 152 and the second tube 154 may be formed of any desired material for use with medical devices, including those materials listed above. In some instances, the first tube 152 and/or the second tube 154 may be a stainless steel hypotube.

The first tube 152 may be fixedly secured to the tubular member 38, while the second tube 154 may be fixedly secured to the elongate wire 40. For instance, the first tube 152 may be fixedly secured to a proximal portion of the tubular member 38 such that the tubular member 38 of the guide catheter 12 extends distally from the rotatable connection 150. In some instances, a proximal portion of the tubular member 38 may extend into and/or through the lumen of the first tube 152 of the rotatable connection 150. The second tube 154 may be fixedly secured to a distal end of the elongate wire 40 such that the elongate wire 40 extends proximally from the rotatable connection 150.

The first tube 152 may include a first flange 156 proximate a first end of the first tube 152 and a second flange 157 proximate a second end of the first tube 152. The second tube 154 may be positioned around the first tube 152 intermediate the first flange 156 and the second flange 157. The first and second flanges 156, 157 of the first tube 152 may restrict longitudinal movement of the second tube 154 relative to the first tube 152.

The first tube 152 may have an outer diameter less than the inner diameter of the second tube 154, providing a clearance fit between the first tube 152 and the second tube 154 when the first tube 152 is positioned through the lumen of the second tube 154. The clearance between the outer diameter of the first tube 152 and the inner diameter of the second tube 154 may aid in rotational movement between the first tube 152 and the second tube 154. The first and second flanges 156, 157 of the first tube 152 may each have an outer diameter greater than the inner diameter of the second tube 154 to prevent the second tube 154 from sliding off the first tube 152. With the second tube 154 positioned between the first and second flanges 156, 157, the second tube 154 may be restrained from being disconnected from the first tube 152.

In some embodiments, the interface between the outer surface of the first tube 152 and the inner surface of the second tube 154 may have a low coefficient of friction to reduce rotational resistance between the first tube 152 and the second tube 154. For instance, in some embodiments, the outer surface of the first tube 152 and/or the inner surface of the second tube 154 may be coated with a lubricious coating providing a low coefficient of friction between the outer surface of the first tube 152 and the inner surface of the second tube 154 to aid in reducing resistance in rotational movement between the first tube 152 and the second tube 154. Some suitable coating materials which may provide a low coefficient of friction include silicone or a fluoropolymer such as polytetrafluoroethylene (PTFE), ethylene tetrafluoroethylene (ETFE) or fluorinated ethylene propylene (FEP). In some instances, the outer surface of the first tube 152 and/or the inner surface of the second tube 154 may include nibs, bumps, ridges, grooves or other surface characteristics to reduce the contact area between the first and second tubes 152, 154. In other embodiments, the first tube 152 and the second tube 154 may be formed to have different cross-sectional shapes to reduce the contact area and/or number of contact points between the first and second tubes 152, 154. For example, the first tube 152 may have a square cross-sectional shape while the second tube 154 may have a circular cross-sectional shape. Thus, the first tube 152 would contact the inner surface of the second tube 154 at discrete contact points to reduce the contact area between the first and second tubes 152, 154.

The rotatable connection 150 may allow the tubular member 38 to rotate independent of rotation of the elongate wire 40 of the guide catheter 12. Thus, during a medical procedure using the drainage catheter delivery system 10, the elongate wire 40 may not become twisted or entangled with a guidewire extending through the lumen 22 of the tubular member 38 and along side of the elongate wire 40 of the guide catheter 12.

Although the rotatable connections have been illustrated as being used to rotatably couple a tubular member to an elongate wire of a guide catheter of a drainage catheter delivery system, it can be appreciated that the disclosed rotatable connections may be incorporated into a variety of other medical devices. For instance, the disclosed rotatable connections may be incorporated into other medical catheter assemblies which may benefit from the ability of a first member to freely rotate relative to a second member during a medical procedure. In some instances, the rotatable connections may provide torque stress relief to a medical device. In some instances, the rotatable connections may allow an elongate tubular member to rotate relative to an elongate wire coupled to the elongate tubular member. Such rotatable connections may be used in a variety of catheters, such as catheters utilizing a pull wire extending along at least a portion of the length of the catheter. Such rotatable connections could also be incorporated in biopsy forceps, graspers, hemoclips, needles, and other medical instruments.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A catheter assembly comprising:
a handle assembly;
a first tubular member coupled to the handle assembly and extending distally therefrom, the first tubular member including a lumen extending therethrough;
a second tubular member having a proximal end disposed within a distal portion of the lumen of the first tubular member; and
an elongate wire coupled to the second tubular member at a rotatable connection positioned within the lumen of the first tubular member, the elongate wire extending proximally from the proximal end of the second tubular member through a proximal portion of the lumen of the first tubular member;
wherein proximal actuation of the elongate wire relative to the first tubular member causes proximal movement of the second tubular member within the lumen of the first tubular member; and
wherein the rotatable connection allows the second tubular member to rotate independently of the elongate wire and freely revolve relative to the elongate wire;
wherein the rotatable connection comprises:
a discrete first tube having an inner diameter and an outer diameter, a distal portion of the first tube being fixedly attached to a proximal portion of the second tubular member; and
a discrete second tube having an inner diameter and an outer diameter, the second tube being disposed around a proximal portion of the first tube and rotatable relative to the first tube, the elongate wire being fixedly secured to the second tube;
wherein the first tube includes a flange extending radially outward from the outer diameter of the first tube at a proximal end of the first tube.

2. The catheter assembly of claim 1, wherein the outer diameter of the first tube is less than the inner diameter of the second tube.

3. The catheter assembly of claim 1, wherein the distal portion of the first tube extends into the second tubular member.

4. The catheter assembly of claim 1, wherein the second tube is positioned between a proximal end of the second tubular member and the flange.

5. The catheter assembly of claim 1, wherein the elongate wire extends through the lumen of the first tubular member to the handle assembly.

6. The catheter assembly of claim 5, further comprising a guidewire extending through the second tubular member and along a distal portion of the elongate wire.

7. The catheter assembly of claim 6, wherein the rotatable connection prevents the elongate wire from entangling with the guidewire.

8. The catheter assembly of claim 1, wherein the rotatable connection allows the second tubular member to rotate independently of the first tubular member.

9. A drainage catheter delivery system comprising:
a handle assembly;
a push catheter extending distally from the handle assembly, the push catheter having a proximal end, a distal end and a lumen extending therethrough;
a guide catheter disposed in the lumen of the push catheter and having a distal portion extending distal of the distal end of the push catheter, the guide catheter including a tubular portion and an elongate wire coupled to the tubular portion at a rotatable connection at a proximal end of the tubular portion within the lumen of the push catheter, wherein proximal actuation of the elongate wire relative to the push catheter causes proximal movement of the tubular portion within the lumen of the push catheter; and
a drainage catheter surrounding a portion of the tubular portion of the guide catheter extending distal of the distal end of the push catheter with a proximal end of the drainage catheter abutting the distal end of the push catheter;

wherein the rotatable connection allows the tubular portion of the guide catheter to rotate independently of the elongate wire of the guide catheter and freely revolve relative to the elongate wire of the guide catheter;

wherein the rotatable connection comprises:
- a discrete first tube having a proximal portion and a distal portion, the distal portion of the first tube being fixedly secured to the tubular portion of the guide catheter; and
- a discrete second tube disposed around the proximal portion of the first tube and rotatable relative to the first tube, the elongate wire being fixedly secured to the second tube;
- wherein the elongate wire is fixed to a circumferential outer surface of the second tube and extends proximally therefrom.

10. The drainage catheter delivery system of claim 9, wherein the tubular portion of the guide catheter has a central longitudinal axis and the elongate wire of the guide catheter has a central longitudinal axis, the central longitudinal axis of the elongate wire being offset from the central longitudinal axis of the tubular portion.

11. The drainage catheter delivery system of claim 9, wherein the second tube is located between the tubular portion of the guide catheter and the flange of the first tube.

12. The drainage catheter delivery system of claim 9, wherein the distal portion of the first tube extends into a lumen of the tubular portion of the guide catheter.

13. The drainage catheter delivery system of claim 9, further comprising a guidewire extending through the tubular portion of the guide catheter and along a distal portion of the elongate wire.

14. A catheter assembly comprising:
- an elongate tubular member having a proximal end, a distal end, a lumen extending from the proximal end to the distal end, and a central longitudinal axis;
- an elongate wire having a proximal end, a distal end and a central longitudinal axis; and
- a rotatable connection rotatably coupling the elongate wire to the elongate tubular member, the rotatable connection including:
  - a discrete first tube having a proximal portion, a distal portion, and a flange extending radially outward from the proximal portion, the distal portion fixedly attached to a proximal region of the elongate tubular member, the proximal portion extending proximal of the proximal end of the elongate tubular member; and
  - a discrete second tube extending proximal of the elongate tubular member and disposed concentrically over an outside surface of the proximal portion of the first tube and being rotatable relative to the first tube, the elongate wire being fixedly attached to an outer circumferential surface of the second tube.

15. The catheter assembly of claim 14, wherein the central longitudinal axis of the elongate wire is offset from the central longitudinal axis of the elongate tubular member.

16. The catheter assembly of claim 14, the second tube being positioned between the proximal end of the elongate tubular member and the flange.

17. The catheter assembly of claim 14, wherein the elongate wire is fixedly attached to the second tube with a saddle extending partially around a circumference of the second tube.

* * * * *